US005853864A

United States Patent [19]
Bunnelle

[11] Patent Number: 5,853,864
[45] Date of Patent: Dec. 29, 1998

[54] COMPOSITE ARTICLE RESISTANT TO MOISTURE-INDUCED DEBONDING

[75] Inventor: William L. Bunnelle, Ham Lake, Minn.

[73] Assignee: H. B. Fuller Licensing & Financing Inc., St. Paul, Minn.

[21] Appl. No.: 492,950

[22] Filed: Jun. 21, 1995

Related U.S. Application Data

[63] Continuation-in-part of Ser. No. 667,251, Mar. 8, 1991, abandoned, which is a continuation of Ser. No. 213,789, Jun. 30, 1988, abandoned.

[51] Int. Cl.$^6$ ........................................................ B32B 7/00
[52] U.S. Cl. ...................... 428/261; 428/264; 428/265; 428/267; 428/475.8; 428/507; 428/516; 428/520; 428/523; 524/293; 524/575
[58] Field of Search .................................. 428/261, 264, 428/265, 267, 475.8, 507, 516, 520, 523; 524/293, 575

[56] References Cited

U.S. PATENT DOCUMENTS

| | | | |
|---|---|---|---|
| 3,615,106 | 10/1971 | Flanagan et al. | 281/21 |
| 3,932,326 | 1/1976 | Hoh et al. | 260/26 |
| 4,028,292 | 6/1977 | Korpman | 260/27 R |
| 4,080,347 | 3/1978 | Hefele | 260/18 N |
| 4,136,699 | 1/1979 | Collins et al. | 128/290 R |
| 4,284,542 | 8/1981 | Boyce et al. | 260/27 R |
| 4,378,445 | 3/1983 | Brasen et al. | 524/284 |
| 4,460,364 | 7/1984 | Chen et al. | 604/387 |
| 4,526,577 | 7/1985 | Schmidt, Jr. et al. | 604/366 |
| 4,622,357 | 11/1986 | Tsuchida et al. | 524/270 |
| 4,627,847 | 12/1986 | Puletti et al. | 604/365 |
| 4,711,683 | 12/1987 | Merkatoris | 156/164 |
| 4,717,749 | 1/1988 | Tang et al. | 524/271 |
| 4,734,447 | 3/1988 | Hattori et al. | 524/271 |
| 4,745,026 | 5/1988 | Tsukahara et al. | 428/323 |
| 4,767,813 | 8/1988 | Evitt | 524/271 |
| 5,026,756 | 6/1991 | Arendt | 524/293 |

FOREIGN PATENT DOCUMENTS

| | | |
|---|---|---|
| 0 154 068 | 9/1985 | European Pat. Off. . |
| 0 156 257 | 10/1985 | European Pat. Off. . |
| 0 249 979 | 12/1987 | European Pat. Off. . |
| 3347294 C1 | 7/1985 | Germany . |
| 3447442 A1 | 8/1985 | Germany . |
| 60-245665 | 12/1985 | Japan . |
| 62-81470 | 4/1987 | Japan . |
| 1193626 | 6/1970 | United Kingdom . |
| PCT/US89/03247 | 2/1990 | WIPO . |

OTHER PUBLICATIONS

"Diphenyl Phthalate (DPP)—Resin Plasticizer, Technical Bulletin O/PL–319", Monsanto.
"Highly–polar, solid plasticizer", Santicizer 3".
Industrial Hygiene, Toxicology and Material Safety Data Sheet.
"Solid plasticizer for nitrocellulose lacquers, vinyls and acrylics—Dicyclohexyl phthalate", Monsanto.
"Plasticizing resin for cellulosic specialties—Santolite MHP", Monsanto.
"Santicizer® 9—Solid Processing Aid and Reactive Plasticizer" Technical Bulletin IC/PL–9, Monsanto
"Solid plasticizer for heat–sealing adhesives and lacquers—Santicizer 1–H".
"Flame–retarding plasticizer for cellulosic materials—Triphenyl Phosphate", Monsanto.
Benzoflex® S–358 Product Bulletin No. 35010–3 dated Feb. 1, 1973, Velsicol Chemical Corporation.
Benzoflex® S–432 Product Bulletin No. 44492 dated Aug. 16, 1971, Velsicol Chemical Corporation.
Benzoflex® S–404 Product Bulletin No. 44490 dated Aug. 15, 1975, Velsicol Chemical Corporation.
Sucrose Benzoate Product Bulletin No. 44200–2 dated Dec. 1, 1978, Velsicol Chemical Corporation.
Benzoflex® S–552 Product Bulletin No. 35070–032 dated Oct. 1977, Velsicol Chemical Corporation.
Market Applications Guide Benzolflex® Plasticizers, Velsicol Chemical Corporation.
"Benzoflex® Plasticizers for Use As Components in Food Packaging Adhesives" Product Bulletin, Velsicol Chemical Corporation.
Benzoflex® S312 Product Bulletin No. 35020 dated Sep. 13, 1982, Velsicol Chemical Corporatio.

*Primary Examiner*—Mark D. Sweet
*Attorney, Agent, or Firm*—Carolyn A. Fischer

[57] ABSTRACT

The articles of this invention have increased resistance to moisture induced delamination at a bond line comprising a substrate, a second layer an dan adhesive. The increased resistance to moisture and increase in bond strength between the adhesive, the substrate and the second layer is produced through a novel adhesive. The adhesive after spraying cools to below the softening point of the components but retains sufficient liquidity to fully wet or to penetrate the second layer causing the layers to be bonded to the film substrate through intimate adhesive bonds or by bonding through a physical entrapment. The physical entrapment of the non-woven layer substantially prevents moisture-induced debonding or delamination.

14 Claims, 3 Drawing Sheets

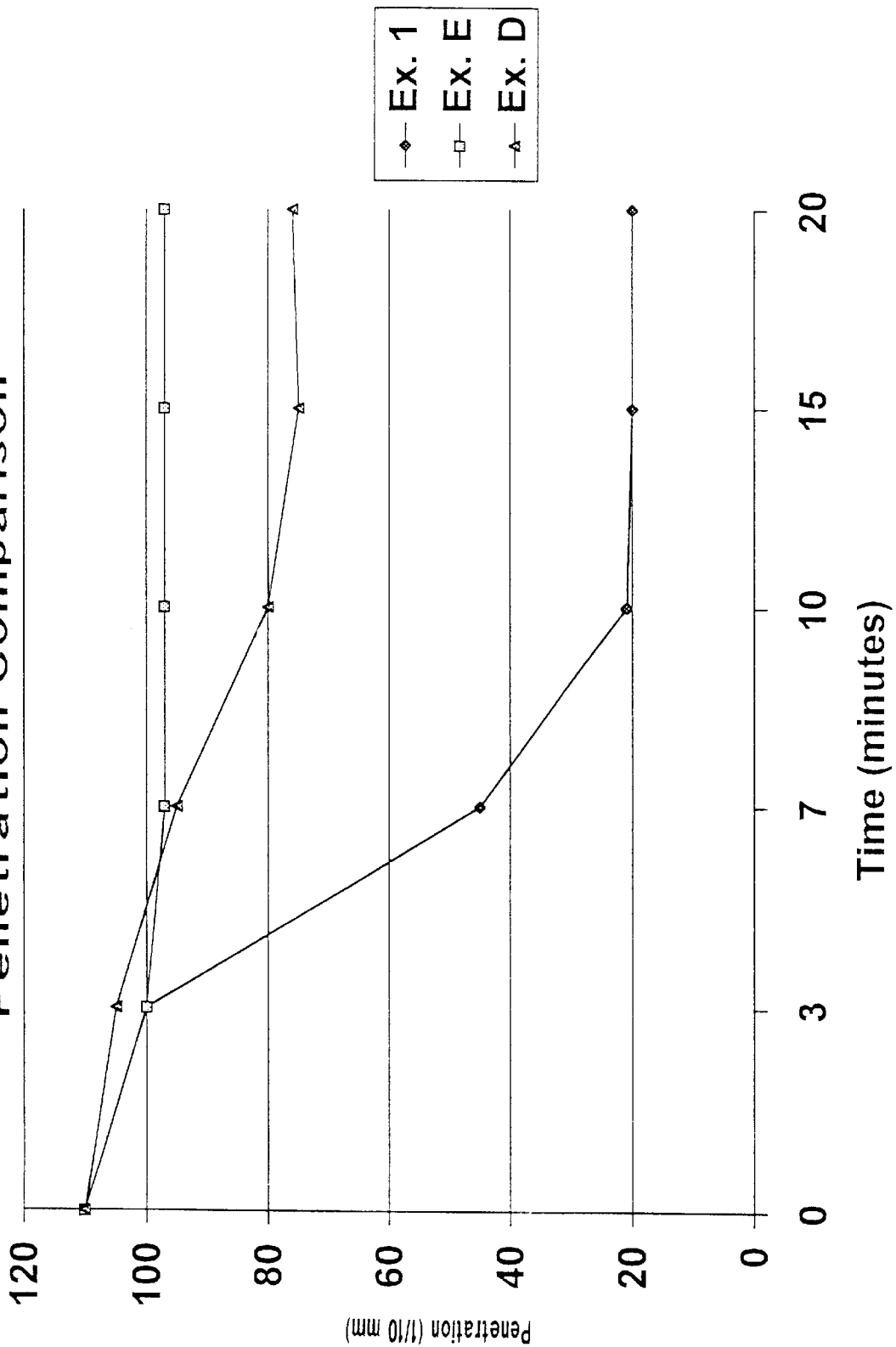

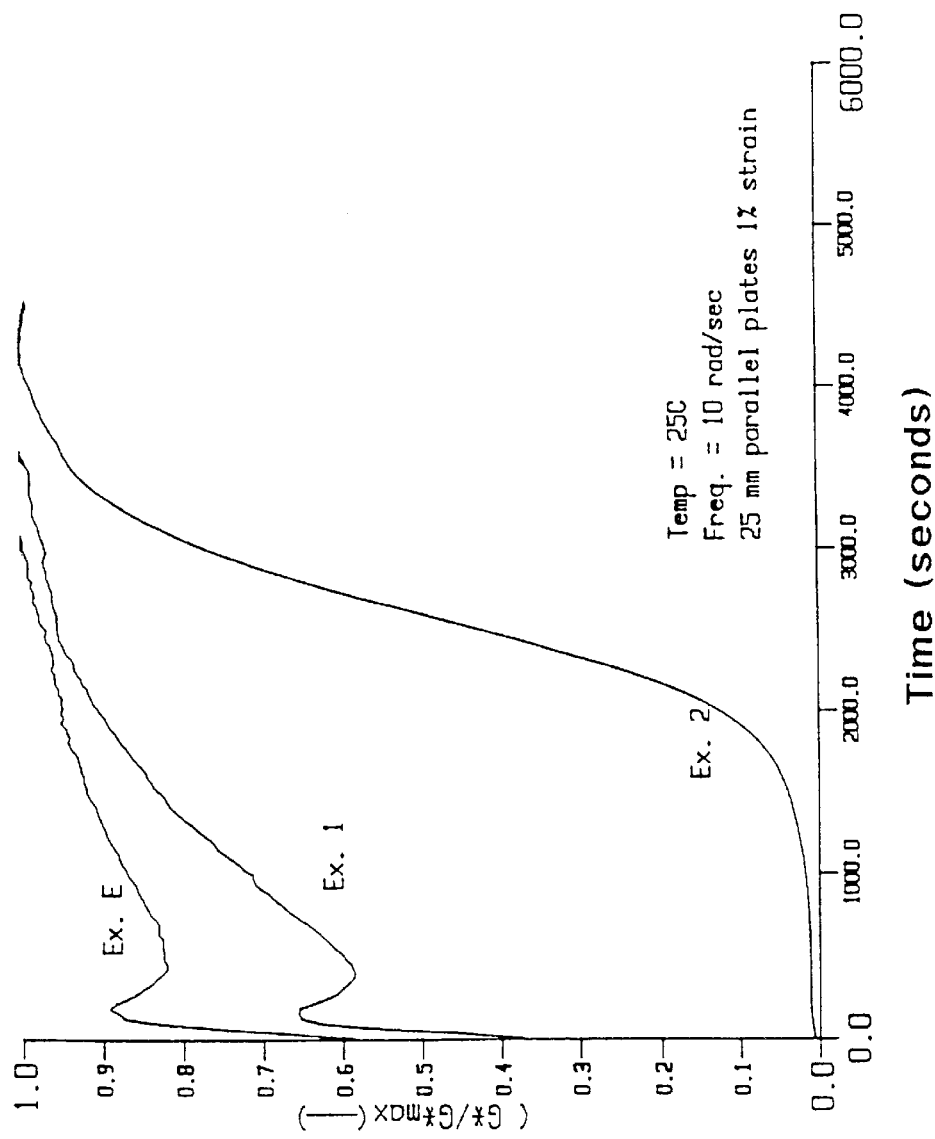

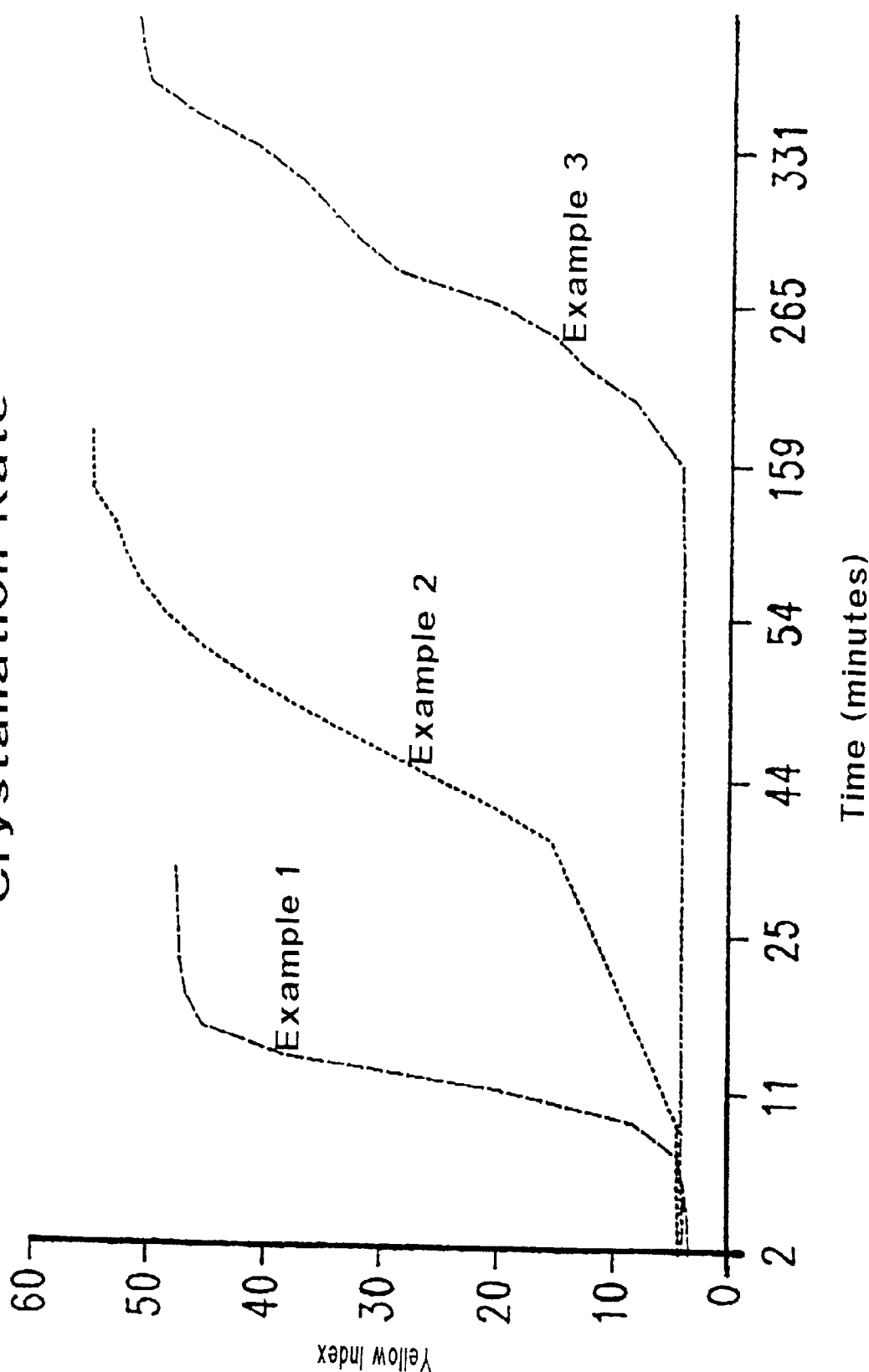

COMPOSITE ARTICLE RESISTANT TO MOISTURE-INDUCED DEBONDING

This application is a continuation-in-part application of U.S. Ser. No. 07/667,251, filed Mar. 8, 1991 now abandoned, which is a file-wrapper-continuation application of U.S. Ser. No. 07/213,789, filed Jun. 30, 1988, now abandoned.

FIELD OF THE INVENTION

The invention relates to a disposable composite article made by joining its components with an adhesive. The invention more particularly relates to disposable articles made by adhesively bonding a film, a woven or nonwoven fabric, tissue or sheet to a substrate using a novel adhesive that can be sprayed on during construction. Still further, the invention relates to the manufacture of a disposable composite article having a covering envelope and an internal absorbent layer, held within the envelope. The envelope can be formed from a porous front sheet adhered to an impervious back sheet and can have further layers added made of a film or fabric. The absorbent layer can be made of tissue, absorbent fiber, or combinations of other absorbents and wrapping layers. Such layers are constructed using the adhesive of the invention to bind the absorbents in a mechanically stable form or to join the outer wrap to the absorbent. The sprayable hot melt adhesive composition typically contains a particular blend of thermoplastic block copolymer, a compatible tackifying resin, and a solid plasticizer.

More particularly, the invention relates to disposable articles such as disposable infant and adult diapers and feminine pads that are resistant to moisture-induced debonding because of the unique qualities of the adhesives of the invention and to novel methods of article manufacture.

BACKGROUND OF THE INVENTION

Disposable articles and their manufacture from construction materials including fabrics, films, and adhesives are described in a variety of United States patents. Korpman, U.S. Pat. No. 4,028,292 teaches a thermoplastic composition which is resistant to heat deterioration at elevated temperatures comprising an oil-insoluble, heat reactive phenol formaldehyde resin and a suitable antioxidant of a metal dithiocarbamate. The only mention of plasticizers at all is in Column 4, lines 64–66, that states: "Plasticizers also may be used to supplement or partially replace the liquid portion of the resin." Collins et al., U.S. Pat. No. 4,136,699 teaches a disposable article using a hot melt pressure sensitive adhesive as a positioning and construction material. Such adhesive, an improvement over Korpman but using a plasticizer oil, is typically extruded at high temperature onto the materials of construction during manufacture. Similarly, Chen et al., U.S. Pat. No. 4,460,364 teaches hot melt pressure sensitive adhesives used in the manufacture of sanitary products. Schmidt, Jr. et al., U.S. Pat. No. 4,526,577 teaches the use of styrene-butadiene-styrene block copolymers in the manufacture of disposable laminates using multiline extrusion adhesive application technology. Puletti et al., U.S. Pat. No. 4,627,847 also teaches the use of hot melt adhesives in disposable article construction. The adhesives disclosed in Collins et al., Chen et al., Schmidt, Jr. et al. and Puletti each use a plasticizing oil, and Puletti teaches that at column 4, lines 1–24, the adhesive can be applied to articles with a variety of conventional methods, including spraying and extrusion. Boyce et al., U.S. Pat. No. 4,284,542 teach hot melt adhesive and sealant compositions based on alkali metal ionomers of random copolymers of ethylene, methyl acrylate, and one or more carboxylated monomers having improved high temperature viscosity stability when the composition contains 0.05–10 parts of ammonium polyphosphate per each one hundred parts of ionomer or resin. Both liquid and solid plasticizers are useful in the compositions of Boyce et al. Only solid plasticizers are useful in the adhesives of the present invention. Tsukahara, U.S. Pat. No. 4,745,026 teaches thermal delayed tack sheets containing an aqueous based adhesive components including a polymer, a solid plasticizer and preferably a tackifier. In Column 1, line 45, the specification states:

"The tackifier is an auxiliary component for increasing tackiness, when activated by heating, and it preferably blended but is not an essential ingredient."

The tackifier of the present invention is an essential component since the tackifier and plasticizer interact to control the crystallization rate of the solid plasticizer, cold flow-open time and final onset of crystallization. An extensive list of solid plasticizers is taught in Tsukahara. However, the list does not include cyclohexane dimenthanol dibenzoate.

In the conventional production of such articles, hot melt adhesives are typically extruded at elevated temperature directly onto a work piece. Additional layers of a nonwoven fabric or film can be adhered through the hot melt adhesive bonds. With extruded hot melt adhesives, disposable articles with mechanical bonding caused by entrapped layers of fabric or tissue can be made because the adhesive can be extruded at high temperature directly on the work piece. The hot extruded adhesive retains sufficient heat that the material remains liquid for a sufficient time such that the adhesive can soak into the fabric or tissue to form entrapping bonds. Additionally, atomized or misted typically aqueous based adhesives have been used in other end uses in which the adhesive is delivered in the form of a spray of finely divided droplets. However, such adhesives have had little or no success in disposable articles.

In recent years, increasing attention has been directed to development of hot melt adhesives that can be sprayed onto the work piece or substrate in a manufacturing regimen. The use of spray-on adhesives have been found to increase productivity. Conventional spray-on adhesives are sprayed from a plurality of narrow orifices in the form of fibers, threads or filaments having a substantially circular cross-section with a diameter of about 0.01 to 0.001 inches. The spray-on adhesive takes on the form of fibers that have substantial surface area in comparison to the mass of the fiber. As a result, the sprayed adhesive fiber cools very rapidly upon contact with the ambient atmosphere. Typically, in the manufacture of disposable articles, after spraying the spray-on adhesives reach ambient temperatures before contacting the work piece or are cooled substantially upon immediate contact with the work piece. This is in sharp contrast to extruded hot melt adhesives that retain a significant amount of heat and can remain melted after application. By ambient temperature, we mean the temperature of the surrounding atmosphere and the temperature of the work piece. In these construction applications, the work piece and the temperature of the manufacturing locus are typically not substantially different. Conventional spray-on adhesives, after application to a work piece, typically take the form of a solid mesh or web which is the result of the combined application of a plurality of adhesive fibers creating a substantially overlapping pattern of threads or fibers of adhesive covering the area of application on the work piece.

With conventional spray adhesive technology, the disposable articles are manufactured by contacting a substrate such as a film or woven or nonwoven fabric with the cooled adhesive web on a second substrate and forming a bond between the substrates or layers by pressure. Such conventional spray-on adhesives form typically a laminated surface-to-surface adhesive bond with the film substrates and the fabric layers. By surface-to-surface bonds we mean a physical bond between the adhesive surface and the surface of a sheet or fiber substrate, wherein mechanical entrapment of the substrate in the adhesive does not make a major contribution to bond strength. Conventional spray-on adhesives, when cooled, form adhesive webs with solid characteristics that have little or no cold flow. After cooling, conventional spray-on adhesives have insufficient liquidity to flow onto and wet the surface of the film or fabric or flow into the fabric to entrap or enmesh the fabric in the adhesive mass. Due to the solid nature of the cooled spray-on adhesive, the conventional adhesives rely upon limited surface bonding to obtain an acceptable level of adhesion.

Such surface bonding can result in a disposable article subject to moisture-induced delamination or debonding. The laminated or composite disposable articles often come into contact with moisture from a variety of sources. Such moisture tends to associate with the fibers of the woven or nonwoven fabric or the surface of other substrates. Such moisture can penetrate limited surface-to-surface adhesive bond between the conventional spray-on adhesive and any substrate or porous layer, weakening the bond and resulting in substantial weakening or failure of the bond. These debonding phenomena can be made significantly worse by the hydrophilicity of the underlying substrate. Hydrophilic substrates are preferred since they promote absorbance of moisture in the disposable article. Additionally, in the manufacture of disposable articles, surfactants can be part of any one component or can be post-added to the composite article after manufacture. while such surfactants can improve water absorbance, such surfactants can also enhance moisture-induced delamination. further, if added to the disposable article after manufacture in the form of an aqueous dispersion or spray, the surfactant can directly enhance moisture-induced delamination.

Such moisture-induced debonding or delamination can be a significant problem in the construction of or the use of disposable diapers, feminine pads, incontinent pads, mattress covers,or any other product in which the article components such as a fabric is joined to a sheet or film substrate through surface adhesive bonds. The physical integrity of the article can be compromised due to adhesive bond failure resulting in waste, inconvenience, embarrassment or discomfort. We believe that the weakness in the bonds between the fabric and the conventional hot melt adhesives results from the fact that, upon application, the conventional spray-on adhesive cools so rapidly that the adhesive forms only limited surface bond and cannot flow onto the surface or into the fabric to enmesh woven or nonwoven fibers to form a more secure mechanical bond.

Accordingly, a substantial need exists in the manufacture of articles from woven or nonwoven fabrics for spray-on adhesive that retains flowability or liquidity and can resist the moisture-induced delamination or debonding of such articles made with a hot melt spray-on adhesive.

BRIEF DISCUSSION OF THE INVENTION

We have found a novel spray-on adhesive composition made from components that interact to produce a composition that, after cooling below the softening points of the components, retains sufficient liquidity, for a sufficient period of time, to permit the adhesive composition to flow onto the surface or to penetrate the constituent parts of a disposable composite article, such as a film, a tissue or a woven or nonwoven fabric, sufficiently to enmesh or entrap sufficient fibers and to create a strong mechanical bond that is not substantially weakened, debonded, or delaminated by moisture. In sharp contrast to the limited surface bonding of conventional spray-on adhesives, the spray-on adhesives of the invention do not merely bond to the limited areas of surface of the fibers in the fabric, but cause the adhesive to flow onto the surface to intimately bond or to enmesh or entrap the fibers of the nonwoven. We have found that the cyclohexane dimenthanol dibenzoate solid plasticizer in the adhesive formulations causes the delay in onset of the formation of strong bonds. The delay in onset, (i.e.) the crystallization rate of the adhesive is controlled by the degree of aromaticity of the resin. An aromatic resin is more compatible with the cyclohexane dimenthanol dibenzoate solid plasticizer in the formulation causing slow crystallization, whereas an aliphatic resin is less compatible causing the resulting composition to crystallize quickly. Aromatic and aliphatic resins are blended or a resin having both aromatic and aliphatic character is used to compound adhesives having intermediate rates of crystallization. As a result, bonds that involve the mechanical entrapment of the fibers, even in the presence of substantial quantities of moisture, resist weakening, debonding, or delamination. By reciting that the spray-on adhesive of this invention substantially reduces the onset of moisture-induced weakening or delamination, we mean that the adhesive bonds formed by the liquidity of the adhesive retain sufficient bond strength, to prevent failure of the adhesive and to maintain an intact article during use while wet. The intimate bonds formed by the spray-on adhesives of the invention are distinguished from the limited surface bonding resent in the prior art by the flowability of the adhesives of the invention. Since the adhesives of the invention retain substantial flowability, bonding is obtained by flowing and fully wetting the surfaces that are combined in the manufacturing processes. In the use of the prior art adhesives, since they become solidified before or immediately after application, they tend to have substantially less flowability and can only bond where applied with little or no cold flow.

BRIEF DISCUSSION OF THE DRAWINGS

FIG. 1 is a graphical representation of penetration data comparing materials of the invention with materials characteristic of the prior art.

FIG. 2 is a graphical representation of the Rheology of materials characteristic of the prior art and the materials of the invention.

FIG. 3 is a graphical representation of the controlled change in crystallization of materials of the invention.

DETAILED DESCRIPTION OF THE INVENTION

Briefly, the nonwoven articles of the invention obtain their substantial resistance to moisture-induced delamination or debonding because a substrate layer is joined with a separate layer through an adhesive that is sprayed on. The adhesives typically comprise a thermoplastic block copolymer such as an A-B-A block copolymer, an A-(B-A)$_n$-B-A, multiblock or tapered block copolymer, wherein n is an integer of about 1 or more, or a radial block copolymer. In the block copolymer, each A comprises a polystyrene block and each B comprises a rubbery block. In addition to the block copolymer, the adhesive contains a tackifying resin which is a rosin acid or rosin ester or is aliphatic or mixed aliphatic-aromatic in character. The adhesive additionally comprises a plasticizer compound that has a softening point that is greater than disposable article manufacturing ambient temperature (typically 25°–35° C.).

We have found that these components cooperate to form an adhesive having improved article assembly properties (low viscosity at application temperatures), but additionally, after spraying and cooling to ambient temperatures, retains a liquid character for a substantial period of time which is sufficient to either fully wet the surface or to penetrate the porous layers. As a result the adhesive retains an extended open time, exhibits a good viscosity profile, and excellent dry and wet bond strength. The adhesive components can be formulated to retain liquid characteristics for a substantial period of time. The adhesive during this liquid period can flow onto the surfaces of the article component to fully wet out the surface creating enhanced bonding resistant to moisture. Additionally, the adhesive during this period of liquidity can flow into, surround and mechanically entrap or enmesh the fibers of a woven or nonwoven fabric or layer. While solidification is delayed, the adhesive, after solidification occurs, has enhanced cohesive strength because of the nature of the components. The use of the phrase sufficient liquidity for sufficient time to form moisture resistant bonds indicates that the adhesive remains liquid (with a viscosity less than 5,000 cP, preferably less than 2,000 cP, most preferably less than 1,000 cP, at 350° F.) with little or no peel strength (less than 50 grams, preferably less than 30 grams) until solidification occurs over a period typically greater than 5 minutes, greater than 10 minutes or greater than 60 minutes, depending on the adhesive used. Since the adhesive remains liquid and does not solidify, it has little peel strength until it solidifies. After solidification the cohesive strength of the adhesive generally exceeds the strength of the materials used in the disposable article.

THE BLOCK COPOLYMER

Thermoplastic block copolymers that can be used in the novel adhesives of the invention in manufacturing disposable articles are thermoplastic rubbers that terminate in hard, glassy end blocks which are thermodynamically incompatible with the rubbery midblocks. such polymers consequently consist of two phases in a solid state, a continuous rubber phase and a substantially discontinuous hard, glassy or plastic phase which locks the rubber molecules in place. The end blocks produce physical crosslinking because the end blocks of a plurality of molecules are joined by physical van der Waals' attraction in a single domain or crosslinked site. Such an interaction forms domains which are stable. The literature describes numerous molecular variations of the thermoplastic rubber copolymers, including the A-B-A structure, an A-B-C structure, a branched or radial configuration and a multiblock or tapered block structure with repeating segments A-(B-A)$_n$-B-A, and so forth, wherein n is an integer of at least 1 to 15.

The A blocks are typically homopolymeric polystyrene. However, other vinyl arene monomers can be used in preparing either a homo or copolymeric plastic or glassy end or A block. the B blocks typically comprise rubbery polymers derived from diene monomers including isoprene and butadiene. The midblocks can be post treated to improve their heat stability through hydrogenation or other treatment. We believe the size and amount of the A or end blocks in conjunction with the time to reform the end block domains is important to the important properties of the invention. As the A blocks increase in size the rate and tendency of the adhesive to solidify increases. We believe this is due to the interaction between the A blocks, the tackifier and primarily the solid plasticizer. Large A blocks or insufficiently plasticized A blocks can rapidly solidify after cooling, can be free of the delayed solidification effect and can have reduced moisture resistance. While the total styrene content of the polymers can be as much as 51 wt-% of the polymer, and since the polymers can have more tan two A blocks for optional performance, the largest A block should be less than or equal to about 15 wt-% of the polymer, and most preferably is less than or equal to 10 wt-% of the polymer. In an S-B-S (styrene-butadiene-styrene) copolymer the preferred molecular weight is about 50,000 to 120,000 and the preferred styrene content is about 20 to 35 wt-%. In an S-I-S (styrene-isoprene-styrene) copolymer the preferred molecular weight is about 100,000 to 150,000 and the preferred styrene content is about 14–30 wt-%. Hydrogenating the butadiene midblocks produces rubbery midblocks that are typically considered to be ethylene-butylene midblocks.

Such block copolymers are available from Shell Chemical Company, Enichem and Fina. Multiblock or tapered block copolymers (the A-(B-A)$_n$-B-A type) are available from Firestone under the STEREON 840A and 845 trademarks.

TACKIFYING RESIN

The adhesives of the invention contain a tackifying resin in combination with a thermoplastic block copolymer and the plasticizer. Tackifying resins useful in the adhesives of the invention comprise rosin derivatives including wood rosin, tall oil tall oil derivatives, rosin ester resins, natural and synthetic terpenes and aliphatic or mixed aromatic-aliphatic tackifying resins.

Aromatic monomers useful in forming the aliphatic-aromatic adhesive compositions of the invention can be prepared from any monomer containing substantial aromatic qualities and a polymerizable unsaturated group. Typical examples of such aromatic monomers including the styrenic monomers styrene, alphamethylstyrene, vinyl toluene, methoxystyrene, t-butylstyrene, chlorostyrene, etc., indene monomers including indene, methyl indene and others. Aliphatic monomers are typically natural and synthetic terpenes which contain $C_5$ and $C_6$ cyclohexyl or cyclopenyl saturated groups that can additionally contain a variety of substantially aliphatic ring substituents. Aliphatic tackifying resins can be made by polymerizing a feed stream containing sufficient aliphatic monomer such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-1,3-butadiene, 2-methyl-2-butene, cyclopentadiene, dicyclopentadiene, terpene monomers and others. Mixed aliphatic-aromatic resins contain sufficient aromatic monomers and sufficient aliphatic monomers and optionally other $C_3$–$C_8$ unsaturated monomers to produce a resin having both aliphatic and aromatic character.

The adhesive compositions of the invention can contain rosin and rosin derivatives as a tackifying agent. Rosin is a solid material that occurs naturally in the oleo resin of pine trees and typically is derived from the oleo resinous extrudate of the living tree, from aged stumps and from tall oil produced as a by-product of kraft paper manufacture. After it is obtained, rosin can be treated by hydrogenation, dehydrogenation, polymerization, esterification and others. Rosin is typically classed as a gum rosin, a wood rosin, and as a tall oil rosin. The materials can be used unmodified and additionally can be used in the form of esters of polyhydric alcohols and can be polymerized through the inherent unsaturation of the molecules. The materials are commercially available and can be blended into the adhesive compositions using standard blending techniques.

Representative examples of such rosin derivative tackifying resins include the pentaerythritol esters of tall oil, gum rosin, wood rosin or mixtures thereof.

Representative examples of such aliphatic resins include hydrogenated synthetic $C_9$ resins, synthetic branched and unbranched $C_5$ resins and mixtures thereof.

Representative examples of such aromatic aliphatic tackifying resins include styrenated terpene resins, styrenated $C_5$ resins or mixtures thereof.

The selection of tackifying resins is based on the nature of the B or midblock of the block copolymer. Rosin derivatives are best for S-I-S/S-B-S blends and can be used with S-I-S or S-B-S along. Hydrogenated $C_9$ or straight aliphatic resins are preferred for S-I-S copolymers. For S-B-S copolymers styrenated terpenes are preferred.

PLASTICIZER

A plasticizer is broadly defined as a typically organic composition that can be added to rubbers and other resins to improve extrudability, flexibility, workability or stretchability. Typical plasticizers in adhesives are plasticizing oils that are liquid at typical ambient temperature. The plasticizer used in the spray-on adhesives of the invention is typically a solid composition having a softening point of at least 45° C. Preferably, the plasticizer composition has a softening point of at least 60° C. Increased softening points (60°–130° C.) can aid in improving heat resistance or preventing bond failure at high temperatures. The selection of plasticizer and the use of small amounts of oil can aid in the control over the time from spraying to solidification. The preferred plasticizers of the invention have some substantial aromatic character. Such aromatic character enables the solid plasticizers to interact with the tackifying resins and the end or A blocks of the thermoplastic copolymer which results in the unique property of the adhesive composition that it retains substantial liquidity for a substantial period of time after cooling below the softening points of the components. The solid plasticizer of the invention retains plasticizing properties during the time it remains in a liquid state prior to adhesive solidification. After solidification the plasticizers can associate with the A or end blocks due to plasticizer aromaticity or can phase out and can no longer interact with an plasticize the polymer units. Once phased out, the plasticizer becomes generally inactive with respect to adhesive properties. After the plasticizer solidifies, the adhesive retains adhesive and cohesive strength through the polymer and tackifying resin regardless of the physical state of the plasticizer. However, the plasticizer, if it does not phase out, can increase cohesive strength of the adhesive after solidification if it associates in the A block phase.

A second class of useful plasticizer comprises an aromatic carboxylic acid ester of a polyfunctional alcohol having 1 to 10 hydroxyl groups. Polyfunctional alcohols that can be used in the compositions of this class of plasticizers include compounds having at least two hydroxyl groups and at least two carbon atoms in the molecule. Specific examples of preferred hydroxy compounds include ethylene glycol, propylene glycol, 1,2-butylene glycol, 1,4-butylene glycol, glycerine, glucose, fructose, sucrose, mannitol, trimethylol ethane, 1,4-cyclohexane dimethanol, pentaerythritol, 2,2-dimethyl-1,3-propane diols, 2-hydroxy methyl-2-methyl-1,3-propane diol, neopentyl glycol, and other useful polyfunctional hydroxyl compounds. Aromatic acids that can be used with the polyfunctional alcohols to form this class ester plasticizer compounds of the invention include aromatic carboxylic acids, typically having at least one aromatic group and at least one carboxyl function. Representative acids include benzoic acid, naphthanoic acid and 4-methyl benzoic acid. Preferred plasticizer comprises 1,4-cyclohexane dimethanol dibenzoate.

In the manufacture of disposable articles, materials or components that are not sufficiently hydrophilic can be treated with surfactants or wetting agents to increase or enhance the wettability or hydrophilicity of the components. Since the disposable articles are designed to absorb and sequester water from the skin of the user of the disposable article, the articles are typically manufactured from hydrophilic materials that absorb and remove water from the surface of the user's skin. However, in certain disposable articles materials that are not sufficiently hydrophilic are used. Such materials include polyolefins, elastics, nonwovens, films, etc. Such materials with measurable hydrophobicity which are not sufficiently hydrophilic can be treated with wetting agents to increase their hydrophilicity. Very often the hydrophobic materials are covers or covering sheets over the hydrophilic materials. To enhance passage of the moisture from the user to the hydrophilic internal layers the hydrophobic cover sheets are made hydrophilic using surfactant or wetting agent materials. Preferred surfactant or wetting materials for use in the invention comprise nonionic surfactants typically manufactured by the oligomerization or polymerization of ethylene oxide or propylene oxide. Such materials typically take the form of polyethylene glycol, polypropylene glycol, ethoxylated or propoxylated alcohols, ethoxylated or propoxylated phenols or other related molecules having as a major polymer backbone polyethylene oxide, polypropylene oxide, or mixtures thereof.

The adhesive compositions of the invention can contain other compatible polymers, fillers, pigments, dyes, catalysts, inhibitors, antioxidants, UV absorbers, waxes, and other conventional additives.

The following Table A sets forth useful proportions of the components of the invention.

TABLE A

|  | Useful | Preferred | Most Preferred |
|---|---|---|---|
| Block copolymer | 10–40 | 12–28 | 15–25 |
| Tackifying resin | 30–80 | 45–75 | 50–65 |
| Plasticizer | 5–40 | 10–30 | 15–25 |

The articles of the invention at a minimum comprise a film layer or a permeable layer adhesively joined with a substrate.

The permeable layer can comprise a cellulosic tissue, a woven or nonwoven fabric or other thin, flexible, porous or wettable sheet-like material. The tissue layer is a well known, typically loosely formed cellulosic sheet of high porosity or permeability. The fabric layer consists of a fluid permeable flexible material that can be made of either hydrophilic or hydrophobic fiber components. Woven and nonwoven webs comprising the fabric can comprise natural or synthetic fibers or mixtures thereof. Woven and nonwoven materials are well known and their construction methods have been practiced for many years. Woven fabrics are typically manufactured in weaving machines forming an interlocking mesh of fibers forming the layer. Nonwoven fabrics can be made through a dry-laid or wet-laid method in carding processes, air laying processes or spun bond processes to produce a web that is mechanically, chemically or thermally formed. The fabric layers for use in the compounds and articles of this invention typically have a basis weight in the range of about 10 to 25, preferably 14 to 18 grams per square yard, a minimum dry tensile strength of at least 800 grams per centimeter$^2$ squared in the machine direction, and at least 200 grams per centimeter$^2$ in a cross machine direction. Synthetic materials commonly used in forming the fabric top sheets include rayon, polyester, polypropylene, polyethylene, nylon and others.

The substrate materials that can be used in the manufacture of the disposable articles of the invention, in combination with the tissue or woven or nonwoven fabric, comprises any typical substrate used in the manufacture of disposable articles including films, sheets, elastics, absorbents, cellulosic fluffs or fill, other tissue, woven or nonwoven fabrics, etc.

Absorbent layers can be adhered to other substrates using the adhesives of the invention. Such absorbent layers can comprise cellulosic pulp or fluff. Such fluff layers are often formed and wrapped in tissue to provide mechanical integrity to the fluff which has little inherent integrity. Fluff is typically manufactured through formation of cellulosic fibers. However, other materials can be utilized to form high absorbent fluff or pulp layers.

Elastic bands or elements can be used in the manufacture of the disposable articles of this invention.

The film or sheet-like layer used in the invention comprises a flexible sheet-like or film substrate. Such films are typically manufactured from thermoplastic resins and take the form of a thin layer having a thickness of about 0.5 to 2.0 mils. Such films comprise polyethylene, polypropylene, ethylene-propylene copolymers, ethylene acrylate copolymers, ethylene vinyl acetate copolymers, polyvinyl chloride polymers, polyvinylidene chloride polymers, polyester polymers and others. Such films can be perforate or imperforate. In addition to the above materials used in the composite articles of the invention, a variety of other materials can be used, including other wrapping materials, deodorants, perfumes, dyes, and decorative appliques, which provide further absorbency, instructional legends, and pleasing appearance or smells.

In somewhat greater detail, the adhesives of the invention can be used in the manufacture of disposable articles including disposable diapers, incontinent devices or diapers, feminine pads, and disposable bed pads by adhering a porous layer to a substrate. The assembly operations that deserve note include adhering a porous nonwoven layer to a back sheet and adhering a tissue layer to an absorbent core.

In the manufacture of absorbents for disposables, it is common to wrap loosely assembled fluff or batts of absorbent material within a tissue overwrap. In such manufacture, the tissue surrounds the absorbent material in an overlapping fashion such that the spray-on adhesive can be applied to the overlap area, causing the adhesive to penetrate the overlap to contact the underlying fluff or batt. The spray-on adhesive in contact with the tissue and absorbent material forms a strong mechanical bond which maintains the tissue wrap and provides mechanical support and integrity to the underlying fluff or absorbent batt material. As a result of using the manufacturing techniques of the invention, the tissue-covered absorbent material obtains substantial mechanical integrity from the adhesive and tissue structure. During use, the tissue and adhesive maintains the fluff or batt in place and prevents movement of the absorbent material resulting in an inappropriate segregation of absorbent material in a small portion of the absorbent article. Such mechanical integrity insures that the absorbent material stays in place to provide absorbency and protection.

In the manufacture of composite articles, the fluid permeable fabric top sheet is adhered to a film back sheet. An absorbent layer can be introduced into the space between the fabric layer and the back sheet. Typically a fluid in contact with the fabric layer passes through the fabric layer and is absorbed and held within the absorbent layer. The absorbent core typically comprises a highly porous, highly absorbent loosely contacted fluff, wrapped or encased within a tissue cover. The absorbent fluff typically has little mechanical integrity. The tissue wrap or cover, once adhered to the fluff, provides the absorbent layer with substantial dimensional integrity preventing the absorbent material from migrating or collecting in an inappropriate portion of the diaper. The tissue wrap ensures that the absorbent material remains evenly distributed within the envelope created by the back sheet and the fabric layer. The manufactured diaper or the components of the diaper can have elastic bands or segments adhesively attached to provide security for the wearer. such elastic bands create a snug fit at the waist and the leg apertures of the disposable articles. The adhesive compositions of the invention can be used to form bonds between the surfaces of the film materials between apertured films and nonapertured films, between tissue and nonwoven or woven fabric layers, between absorbent fluff and tissue overwraps, and between elastic bands or elements and any structural component of the disposable diaper.

In construction methods for the preparation of the disposable articles of the invention, the adhesives are typically applied from spray heads that deliver the adhesive at elevated temperatures (typically above about 250° F. and typically in the range of 275°–400° F.). The spray heads have apertures that range from about 0.01 to about 0.04 inches. Under the operating conditions of typical adhesive spray machines, the diameter of the sprayed adhesive fiber can range from the size of the aperture to as little as about 0.001 inches depending on operating conditions. Depending on the end use and final bond strength desired, the adhesive can be used at application amounts that range from 0.5 milligrams per square inch to as much as 10 milligrams per square inch. preferably, because of the unique properties of the adhesives of this invention, the adhesives can be used at an application amount of from about 0.5 milligrams per square inch to 5 milligrams per square inch. Conventional spray-on adhesives are typically used at high add-on rates within a range of 6 to 7 milligrams per square inch because of their tendency to debond or delaminate in the presence of moisture. The conventional add-on rate appears to be excessive because bonding characteristics of the adhesives are poor. Most preferably, in disposable diaper construction the adhesive of the invention is used at an application rate of about 1 to about 4 milligrams per square inch.

During the manufacture of disposable articles using the adhesives of the invention, two modes of application are preferred. One mode of operation involves spraying the adhesive upon a fabric, such as a tissue, a woven or nonwoven web, or other material having permeability to the adhesive. Such sprayed-on adhesive can penetrate the permeable tissue, nonwoven or woven fiber, to cause the sheet to be embedded in the adhesive and adhered to the substrate such as an absorbent layer, back layer, or film. Alternatively, the adhesives of the invention can be directly applied to back sheet or film and the tissue, woven or nonwoven fabric, or other material can be applied to the adhesive on the film. The adhesive retains sufficient liquidity that it can penetrate pores or apertures in the fabric to form a mechanical bond. In the manufacture of tissue fluff absorbent cores, the fluff is typically wrapped by tissue. the tissue layer can be wrapped around the fluff and can overlap. Adhesive can then be sprayed on the overlapping portion of tissue outerwrap, can penetrate the wrappings and adhere the tissue to the fluff ensuring that the fluff obtains dimensional stability from adherence to the outer wrap.

In somewhat greater detail, the sprayable, hot melt adhesive compositions of the invention typically comprise an effective amount of a thermoplastic block copolymer base and an effective amount of a tackifying agent and sufficient solid plasticizers to form an effective adhesive that has the unique property that after spraying and cooling retains sufficient liquidity to penetrate a porous layer.

The hot melt adhesives of the invention are made in common hot melt manufacturing equipment. In the manufacture of the hot melt adhesives of the invention, the thermoplastic block copolymers typically added to a melt comprising either the tackifier or the plasticizer material or mixtures thereof. Such additions facilitate the blending of the block copolymer into a smooth, uniform mixture. In such a manufacturing regimen, either the tackifier or the plasticizer or a portion thereof is added to the manufacturing equipment under inert atmosphere and is heated and agitated until melted. The thermoplastic block copolymer is then added to the melt at a rate such that the mixture forms a uniform smooth blend within a reasonable period. Antioxidant materials used in the manufacture of the adhesive can be added to the melt prior to, with, or after the addition of the block copolymer. Once a smooth blend of the copolymer in conjunction with an adhesive component is formed, the balance of the components of the hot melt adhesives can be added at a convenient rate. Once the uniform blend of all the adhesive ingredients is formed, the adhesive can be drawn off and packaged in a convenient form including in drums, blocks, pillows, pellets, granules, etc.

The following examples provide additional information with respect to the manufacture of the adhesives of the invention and include the best mode.

Following the standard laboratory blending procedures the following compositions were blended into a hot melt adhesive:

EXAMPLE I

Into a sigma blade mixer having a nitrogen atmosphere and heated to a temperature of 350° F. was added about 100 grams of 500 processing oil (PENZOIL) and 5 grams of an antioxidant (IRGANOX 1010). The mixer was operated until the antioxidant was fully blended with the oil. Into the oil was added 200 grams of a styrene-isoprene-styrene block copolymer having 25 wt-% styrene (EUROPRENE SOL T193B, Enichem). After the copolymer had been fully added to the resin and a uniform melt resulted, 445 grams of the tackifying resin (ECR 177, Exxon) was slowly added to the mixer followed by 250 grams of a cyclohexane dibenzoate plasticizer (BENZOFLEX 352, Velsicol). The single blade mixer was continued until the contents were a smooth melt blend and the material was withdrawn and packaged.

| Ingredient | Trade Name | PHA[1] |
| --- | --- | --- |
| S-I-S block copolymer | Europrene 193B | 20 |
| Antioxidant | IRGANOX 1010 | 0.5 |
| Hydrogenated $C_{10}$ Tackifying resin | ECR 177 | 44.5 |
| 500 Processing Oil | | 10 |
| cyclohexane dimethanol dibenzoate | BENZOFLEX 352 | 25 |

[1]PHA = parts by weight per each one hundred parts of adhesive

EXAMPLE II

Following the procedure of Example I the following compositions were blended into a hot melt adhesive:

| Ingredient | Trade Name | PHA[2] |
| --- | --- | --- |
| S-I-S block copolymer | Europrene 193B | 20 |
| Antioxidant | IRGANOX 1010 | 0.5 |
| Rosin Ester Tackifying Resin | Unitac H-100 | 22.25 |
| Hydrogenated $C_{10}$ Tackifying resin | ECR 177 | 22.25 |
| 500 Processing Oil | | 10 |
| cyclohexane dimethanol dibenzoate | BENZOFLEX 352 | 25 |

[2]PHA = parts by weight per each hundred parts of adhesive

EXAMPLE III

Following the procedure of Example I the following compositions were blended into a hot melt adhesive:

| Ingredient | Trade Name | PHA[3] |
| --- | --- | --- |
| S-I-S block copolymer | Europrene 193B | 20 |
| Antioxidant | IRGANOX 1010 | 0.5 |
| Rosin Ester Tackifying Resin | Unitac H-100 | 33.375 |
| Hydrogenated $C_{10}$ Tackifying resin | ECR 177 | 11.125 |
| 500 Processing Oil | | 10 |
| cyclohexane dimethanol dibenzoate | BENZOFLEX 352 | 25 |

[3]PHA = parts by weight per each one hundred parts of adheive

EXAMPLE IV

| Ingredient | Trade Name | Grams |
| --- | --- | --- |
| S-I-S block copolymer | KRATON-1117 | 20.0 |
| Tackifier | PERMALYN 305 | 59.8 |
| 1,4-cyclohexane dimethanol dibenzoate | BENZOFLEX 352 | 20.0 |
| Antioxidant | IRGANOX 1010 | 0.2 |

COMPARATIVE EXAMPLE A

Following the procedure of Example I, 155 grams of a hydrogenated Cg tackifying resin (ESCOREZ 5320) and 25.5 grams of a 50—50 blend of antioxidants (IRGANOX 1010 and IRGANOX 1076) was blended in the sigma mixer followed by 127.5 grams of a styrene-ethylene-butylene-styrene block copolymer having 30 wt-% styrene (KRATON G 1652, Shell Chemical Co.). 309.95 grams of the tackifying resin was then blended into the melt followed by 255 grams of a naphthenic oil (SHELLFLEX 371).

COMPARATIVE EXAMPLE B

Following the procedure of Comparative Example A the following compositions were blended into an adhesive:

| Ingredient | Trade Name | Grams |
|---|---|---|
| Atactic poly alpha olefin | B3A15 | 425 |
| Dicyclohexylphthalate plasticizer | DCHP | 85 |
| Tackifying resin | WINGTACK EXTRA | 318.75 |
| Antioxidant | IRGANOX 1010 & IRGANOX 1076 | 4.25 |
| Polyethylene | EPOLENE C10 | 17.0 |

COMPARATIVE EXAMPLE C

Same as Comparative Example A except Shellflex oil was omitted and 549.95 grams of tackifying resin and 170 grams of DCHP were used.

COMPARATIVE EXAMPLE D

Same as Example V except DCHP was omitted and an equal amount of a plasticizing oil (1200 ACS) was used.

COMPARATIVE EXAMPLE E (Column 15, Example 5, Tsukahara et al., U.S. Pat. No. 4,745,026)

| Ingredient | Trade Name | Grams |
|---|---|---|
| Resin | EVA 28-400 | 33.0 |
| Dicyclohexylphthalate plasticizer | MORFLEX 150 | 49.5 |
| Rosin ester tackifying resin | UNITAC H-100 | 17.0 |
| Antioxidant | IRGANOX 1010 | 0.5 |

Detailed Discussion of the Drawings

FIG. 1

FIG. 1 shows a Penetration Comparison in which both the Comparative Examples D and E change very little in penetration as a function of time. Such adhesives become viscous and reach their maximum hardness soon after reaching room temperature. In contrast, adhesives of the present invention remain fluid for a controlled period of time and later crystallize, reaching their maximum strength once fully crystallized.

Determining the Needle Penetration of Hot Melt Adhesives

Scope:
The needle penetration test is used as a measure of consistency. Higher values indicate softer consistency and lower values indicate harder consistency.
Reference:
ASTM D5

Material and Equipment:
1. Standard ASTM Needle Penetrometer
2. Automatic Dwell Timer or stop watch
3. Environmental Chamber Sample Preparation:
Sample must be of sufficient depth so that the needle, when fully penetrated, is only touching sample and not the substrate beneath the sample.

Procedure:
1. Sample was melted at 300° F. and poured into an appropriately sized mold.
2. Load penetrometer with 100 g (shaft and needle weight inclusive).
3. Position needle lightly on the sample surface.
4. Release shaft for 5±0.1 seconds.
5. Clean shaft, repeat steps 3 and 4, etc.

Report:
The penetration is the average of 3 or 5 readings and is reported in tenths of a millimeter, noting the temperature.

FIG. 2

FIG. 2 shows Rheology Curves. Comparative Example E maintains a relatively constant strength as a function of time, whereas adhesives of the present invention gain strength until such adhesives have fully crystallized.

The increase in shear modulus as a result of crystallization is shown in FIG. 2. The ratio of the complex shear modulus, $G^*$ to its maximum value is plotted versus time. $G^* \cdot 10^{-7}$ is shown in FIG. 2. The fast crystallizing melt, Example 1, approached its maximum stiffness in approximately 45 minutes. The medium crystallizing melt, Example 2, approached its maximum level in approximately an hour. The modulus of the amorphous Example E does not change. ($G_{norm}$ is $G^*/G_{initial}$)

Testing:
A two step dynamic time sweep on the Rheometrics RDS 7700 was used to obtain the data. The sample was loaded between 25 mm diameter parallel plates and heated to 120° C. until the sample completely lost any white coloration due presumably to crystallinity. The temperature was then lowered to 90° C. and the loaded sample was allowed to equilibrate for 5 minutes. The test at a frequency of 10 radians/sec was then started. The first stage of the test lasted 5 minutes. The temperature of the liquid nitrogen controlled oven was lowered from 90° C. to 23° C. (The temperature of the plates was note forced to reach 23° C. by lowering the oven set temperature below 23° C.—this would have resulted in faster recrystallization due to the removal of latent heat.) The final stage of the test lasted either one or two hours. The temperature control was deactivated for this segment of the test so that any additional cooling of the sample would occur only due to natural convection with the ambient air. The sample was strained dynamically constantly throughout the test. The gap between the plates occupied by the sample was periodically reduced to compensate for sample shrinkage.

FIG. 3

FIG. 3 are Crystallization Curves that demonstrate the ability to control the rate at which the adhesive crystallizes. The adhesives of the present invention are very fluid and transparent at first. As the cyclohexane dibenzoate plasticizer crystallizes the adhesive becomes opaque. The rate of crystallization is controlled by the selection of tackifying resin. An aromatic resin, such as Unitac H-100 is very compatible with the dibenzoate plasticizer slowing down the crystallization rate, whereas an aliphatic resin is less compatible allowing the dibenzoate plasticizer to crystallize relatively quickly. All formulations remain fluid and cold flow for a controlled period of time and reach their maximum strength upon crystallization.

Measurement of Crystallization Time Using Percent Reflectance

This test method describes how to measure crystallization time of a hot melt as measured by the Hunter Colorimeter to detect changes in reflectance of the hot melt as it cools, crystallizes and becomes opaque. We find that the opaque character is proportional to degree of crystallinity.

Material and Equipment
1. Hunter Colorimeter, Model D25A, with reduced area illumination
2. Black color tile
3. Y of the XYZ scale
4. Half-pint metal can
5. 300° F. vacuum oven capable of a minimum of 20 inches of Hg
6. Mylar film
7. Can opener
8. Ruler and graph paper
9. Scale
10. Half-pint glass jar
11. 60-minute timer
12. Stop watch Procedure
1. Warm up Hunter Colorimeter for 15 minutes.
2. Standardize the Colorimeter using the method described in the Hunter manual.
3. Place between 50–70 grams of hot melt in a half-pint glass jar and put the jar in a 300° F. oven for 60 minutes under 20–30 inches of Hg.
4. Cut out two 5×5 in Mylar squares.
5. Use a can opener to remove the top ring of a quarter-pint can.
6. Place one of the Mylar squares on a scale, put the ring from the half-pint can on top of the Mylar square.
7. Remove the jar of hot melt from the oven and start the stopwatch. Pour 11 grams of hot melt into the can ring and place the second Mylar square on top of the hot melt.
8. Place the sample over the specimen port of the Colorimeter.
9. Place the black tile over the sample.
10. Press the XYZ button and then read button of Colorimeter.
11. Record the Y value and the time every five minutes until the reading stabilizes, which should be somewhere between 40 and 50.
12. Graph the Y value vs. time and use triangulation to determine crystallization point.

Moisture Resistance Test for Spray Applied Hot Melt Adhesives

The test method is intended to assist in determining the differences in wet and dry bond strengths of spray applied hot melt adhesives.

Equipment
1. High quality hot melt spray equipment intended for the nonwoven industry. Preferred equipment manufacturers are Nordson, Acumeter, Slautterback, and Mercer.
2. Tensile tester or T-peel tester with a load range of 1,000 grams and capable of a grip separation rate of 6 inches/minute.
3. Cutting board of 1"×6" cutting template.
4. Suitable substrates.
5. Purified water.

Sample Preparation
1. Spray apply the adhesive to one substrate at the rate of 4 mg./sq. in. Quickly nip the second substrate to the adhesive using a nip pressure of 1.4 (20 psi). If the bond is expected to give substrate failure, slip in 5–10 pieces of 2" wide release paper across the bond line.

Make sure the spray pattern is as even as possible since small variations in coat weight can cause unexpectedly large variations in peel values.

2. Cut a 1"×6" sample out of the laminated area in the machine direction. If release paper was used, cut it in half in the cross direction and then cut 6" strips in the machine direction. Peel back 1" (or use the 1" release paper edge) and apply staples to both substrates to assist gripping. Make ten samples.

3. Condition the samples at room temperature and 50±10% RH for at least 16 hours, but not more than 30 hours.

Test Procedure
1. Set the peel tester to the gram scale 6 inches/minute, 25 seconds.
2. Dry delamination—clamp the substrates into the peel tester. Generally, the weaker substrate will be clamped to the moving grips. Set the position so that there is tension on the adhesive. Turn the peel tester on. Peel a total of five samples.

Wet Delamination—place the 6" sample vertically into five inches of water. Leave in water for 30 seconds (longer if the substrates do not readily absorb water). Pat dry with paper towels. Attach the substrates to the clamps as described above. Set the position so that there is tension on the adhesive. Turn the peel tester on. Peel a total of five samples.

Report
Average peel strength of the dry and wet samples. Note the type of failure that occurred. also, report coat weight, application temperature, substrates used, and spray equipment used. Also note if water soak was longer than specified, or if more time was necessary after application to allow the adhesive to recrystallize completely.

Test Results Comparative Examples

Example A: Dry: good pull; some fiber tear.
Wet: adhesive failure.

Example B: Dry: weak bond.
Wet: no bond.

Example C: Dry: no bond to substrate.
Wet: no bond to substrate.

Example D: Dry: substrate failure.
Wet: 34 grams.

Test Results Examples of the Invention

Example IV: Dry: cohesive failure if pulled slowly—tissue failure if pulled fast;
Wet: excellent bond tissue failure—wet with nonionic surfactant weaker bonds but tissue failure if pulled fast.

The Examples and data shown above indicate that the use of a solid plasticizer such as cyclohexane dimenthanol dibenzoate in combination with a particular selection of block copolymer and tackifying resin can produce an adhesive having both dry and wet bond strength to both film and porous substrate. The comparative Examples indicate that polymers that are not block copolymers and adhesives containing plasticizers other than those similar in properties to cyclohexane dimenthanol dibenzoate do not possess significant wet strength, and in some cases have poor dry strength. Additionally we have found that a blend of S-I-S and S-B-S copolymers can, in certain formulae, provide enhanced wet and dry bonding properties.

Since many embodiments of the invention set forth above can be made without departing from the spirit and scope of the invention, the above specification, Examples and data are non-limiting and the invention resides in the claims hereinafter appended.

We claim:

1. An article resistant to moisture-induced debonding comprising a substrate joined with a second layer by a sprayed-on adhesive, said adhesive comprising:
   (a) about 10–40 parts by weight of a thermoplastic block copolymer selected from the group consisting of an A-B-A block copolymer, an A-(B-A)$_n$-B-A block copolymer, wherein n is an integer of about 1 or more, and a radial block copolymer, each A comprising a polystyrene block and each B comprising a rubbery block;
   (b) about 30 to 75 parts by weight of a tackifying resin selected from the group consisting of a rosin derived tackifying resin, an aliphatic tackifying resin, a mixed aromatic-aliphatic tackifying resin, and mixtures thereof; and
   (c) about 5 to 40 part by weight of a cyclohexane dimethanol dibenzoate plasticizer compound; and wherein, after the adhesive is sprayed on and cooled to ambient temperature, the adhesive retains sufficient liquidity for a sufficient time to wet or to penetrate the substrate or the second layer to form a moisture-resistant bond.

2. The article of claim 1 wherein the adhesive, when cooled, obtains a wet or dry peel strength of less than 50 grams for at least 5 minutes and after solidification obtains a peel strength greater than 100 grams.

3. The article of claim 1 wherein the substrate comprises a film, and the second layer comprises a nonwoven fabric, and the fabric is entrapped by the adhesive.

4. The article of claim 1 wherein both the substrate and second layer comprise films.

5. The article of claim 1 wherein the substrate is a mass of absorbent fiber, the second layer is a tissue overwrap, and both the substrate and the second layer are entrapped by the adhesive.

6. The article of claim 3 wherein the film comprises a polyethylene film, a polypropylene film, a nylon film, a polyvinylidene chloride film, a polyvinyl chloride film, or a polyester film.

7. The article of claim 1 wherein the thermoplastic block copolymer comprises an A-B-A block copolymer having a polyisoprene midblock with a molecular weight of about 100,000 to 150,000 and a styrene content of about 14 to 30 wt-%.

8. The article of claim 1 wherein the thermoplastic block copolymer composition comprises an A-B-A block copolymer having polybutadiene midblock with a molecular weight of about 50,000 to 120,000 and a styrene content about 20 to 35 wt-%.

9. The article of claim 1 wherein the article also comprises a surfactant.

10. The article of claim 8 wherein the tackifying agent is a styrenated terpene.

11. The article of claim 7 wherein the tackifying resin is an aliphatic tackifying resin.

12. The article of claim 1 wherein the block copolymer comprises a blend of a styrene-isoprene-styrene polymer and a styrene-butadiene-styrene copolymer at a weight ratio of about 2 to 5:1.

13. The article of claim 1 wherein the rosin derivative comprises a pentaerythritol ester of a rosin acid.

14. The article of claim 12 wherein the tackifier comprises a wood rosin derivative.

* * * * *